United States Patent [19]
Vilkov et al.

[11] Patent Number: 5,807,579
[45] Date of Patent: Sep. 15, 1998

[54] PSEUDOEPHEDRINE COMBINATION PHARMACEUTICAL COMPOSITIONS

[75] Inventors: Zalman Vilkov, Dingman Ferry, Pa.; David John Willoughby, Wynn Vale; Eugene Quinn, Prospect, both of Australia

[73] Assignee: F.H. Faulding & Co. Limited, Parkside, Australia

[21] Appl. No.: 746,666

[22] Filed: Nov. 14, 1996

[51] Int. Cl.⁶ .............................. A61K 9/26; A61K 9/32; A61K 9/34
[52] U.S. Cl. ........................... 424/469; 424/481; 424/482
[58] Field of Search ................... 424/464, 469, 424/481, 482

[56] References Cited

U.S. PATENT DOCUMENTS

| | | | |
|---|---|---|---|
| 4,975,426 | 12/1990 | Sunshine et al. | 514/159 |
| 4,996,061 | 2/1991 | Webb et al. | 424/475 |
| 5,032,406 | 7/1991 | Dansereau et al. | 424/472 |
| 5,314,697 | 5/1994 | Kwan et al. | 424/480 |
| 5,338,550 | 8/1994 | Edgren et al. | 424/472 |
| 5,368,861 | 11/1994 | Ushimara et al. | 424/472 |

OTHER PUBLICATIONS

*Pharmaceutical Technology Europe*, Feb. 1994, "Development and Industrial Scale–Up of Tablets Containing Modified–Release Pellets", pp. 19–25.

*Primary Examiner*—Peter F. Kulkosky
*Attorney, Agent, or Firm*—Cohen, Pontani, Lieberman & Pavane

[57] ABSTRACT

A pharmaceutical tablet composition for oral administration containing pseudoephedrine pellets admixed with a tablet mixture containing a second active drug substance, either alone or in combination with pseudoephedrine or a pharmaceutically acceptable salt thereof, is disclosed. The pellets provide an extended release of pseudoephedrine, whereas the tablet mixture provides an immediate release of the second active drug and any pseudoephedrine.

14 Claims, No Drawings

PSEUDOEPHEDRINE COMBINATION PHARMACEUTICAL COMPOSITIONS

RELATED APPLICATIONS

This application claims priority from U.S. provisional application Ser. No. 60/006,865 filed on Nov. 16, 1995.

BACKGROUND OF THE INVENTION

1. Field of the Invention

The present invention relates to a pharmaceutical tablet composition for oral administration comprising extended-release pseudoephedrine together with a second active drug in an immediate release form.

2. Description of the Related Art

Pharmaceutical compositions containing a plurality of active ingredients are well known. One commercially available product is Hoechst Marion Roussel's SELDANE-D® which is a tablet comprising the antihistamine, terfenadine, in combination with the nasal decongestant, pseudoephedrine hydrochloride. This product is disclosed in U.S. Pat. No. 4,996,061. This patent teaches a multiple-compression tablet comprising a first discrete zone which provides a sustained release of pseudoephedrine hydrochloride, and a second discrete zone which provides an immediate release of terfenadine in combination with pseudoephedrine hydrochloride. In effect the final composition is an extended-release pseudoephedrine tablet enveloped in or layered with a terfenadine/pseudoephedrine hydrochloride immediate release tablet.

Another commercially available product is Schering's CLARITIN®-D which is a film-coated extended-release tablet composition comprising pseudoephedrine sulfate in a specific polymer matrix core and a film coating on the core, the film coating containing the nonsedating antihistamine, loratadine. This composition, disclosed in U.S. Pat. No. 5,314,697, provides immediate release of loratadine and extended release of pseudoephedrine sulfate from the matrix core over a period in excess of 12 hours.

Extended-release tablets, however, are not always considered an ideal dosage form. One reason is that due to their size, they may not always pass through the stomach to the small bowel promptly, reliably and predictably. Another reason is that extended-release tablets have relied on the tablet being retained as an intact tablet for a substantial period of time. People with aggressive gastrointestinal tracts, however, tend to process the tablets more quickly and so receive a rapid release of the drug instead.

A paper entitled "Development and Industrial Scale-Up of Tablets Containing Modified Release Pellets", Phar Tech. Eur., (February 1994), discloses modified-release pellets of theophylline in tablets which exhibit flash disintegration, and is hereby incorporated by reference. This paper outlines some difficulties experienced with tableting pellets and concludes that inert granules with a particle size distribution similar to the pellets are needed in order to obtain a uniform blend.

SUMMARY OF THE INVENTION

It is therefore an object of the present invention to provide an extended-release tablet composition which alleviates at least some deficiencies of the prior art and allows efficient and controlled absorption and bioavailability of the contained medicaments after oral administration thereof.

It is another object of the invention to provide a pseudoephedrine tablet composition comprising pseudoephedrine pellets blended with a mixture of ingredients including a second active drug, optionally in combination with pseudoephedrine, and compressed into tablets for oral administration.

It is a further object of the invention that the pellets within the tablets provide an extended release of pseudoephedrine, whereas the tablet mixture provides an immediate release of the second active drug, optionally in combination with pseudoephedrine.

Accordingly, the present invention is directed to a pharmaceutical tablet composition comprising pseudoephedrine pellets and a tablet mixture containing a second active drug, a powdered cellulose, a bicarbonate or carbonate, and, if desired, one or more inert ingredients but no anionic or nonionic surfactants, and, optionally, pseudoephedrine, wherein the pellets and tablet mixture are combined and compressed into tablets for oral administration. The pellets provide an extended release of a therapeutically effective amount of pseudoephedrine, whereas the tablet mixture provides an immediate release of a therapeutically effective amount of the second active drug and, optionally, a therapeutically effective amount of pseudoephedrine.

The tablet composition of the present invention does not need to stay intact for substantial periods for extended release to be achieved and leads to more reliable and predictable release profiles.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

The present invention relates to a pharmaceutical tablet composition for oral administration comprising a combination of extended-release pseudoephedrine, or a pharmaceutically acceptable salt thereof, and a second active drug in an immediate release form.

The second active drug is preferably an antihistamine such as, for example, azatadine, loratadine, terfenadine, astemizole, chlorpheniramine, brompheniramine, acrivastine, hydroxyzine, pheniramine, diphenhydramine, mebhydroline, cyproheptadine, promethazine, dexchlorpheniramine, cetirzine, triprolidine, and pharmaceutically acceptable salts thereof.

As used herein, the term "pellets" means those pharmaceutical-containing particles having a diameter from about 300 to about 1500 microns in size. The term "extended-release" is as expressed in the U.S. Pharmacopeia (USPXXIII)(1995), page 1951, and refers to a property of the pharmaceutical composition wherein the contained active medicament is made bioavailable over an extended period of time following ingestion. The term "immediate release" refers to a property of the pharmaceutical composition wherein the entire dose of active medicament is made bioavailable without substantial delay.

As used herein, the term "therapeutically effective amount" of a drug refers to that amount which produces the desired therapeutic response upon oral administration and can be readily determined by one skilled in the art. In determining the therapeutically effective amount, a number of factors are considered, including but not limited to: the particular compound administered, the bioavailability characteristics of the pharmaceutical composition administered, the dose regimen selected, and other relevant circumstances.

(I) Tablet Mixture

The tablets of the pharmaceutical composition comprise the extended-release pseudoephedrine pellets and a tablet mixture containing the second active drug, either alone or in combination with pseudoephedrine.

It is essential that during the compression stage of the tableting, the extended-release pellets are not damaged such that the extended-release character of the pellets are detrimentally affected.

In a preferred embodiment, the tablet mixture comprises a therapeutically effective amount of the second active drug, either alone or in combination with a therapeutically effective amount of pseudoephedrine or a pharmaceutically acceptable salt thereof; a bicarbonate or carbonate, preferably sodium bicarbonate, in an amount from about 1% to about 15% by weight of the tablet composition; and a powdered cellulose in an amount from about 10% to about 50% by weight of the tablet composition.

Representative examples of powdered cellulose include ELCEMA P-100, ELCEMA G-250, and SOLKA-FLOC BW-40. The preferred powdered cellulose is SOLKA-FLOC BW-40.

The tablet composition of the present invention can optionally contain one or more other therapeutically inert ingredients such as are well known and appreciated in the art of pharmaceutical science. Such therapeutically inert ingredients include: binders such as pregelatinized starch, povidone, cellulose derivatives including methylcellulose, hydroxypropyl methylcellulose, and the like; conventional carriers and fillers such as lactose, corn starch and the like; lubricants such as magnesium stearate, calcium stearate, zinc stearate, stearic acid, talc, hydrogenated vegetable oil and the like; glidants such as silicon dioxide and the like; disintegrants such as croscarmellose sodium, corn starch derivatives (e.g., starch glycolate sodium) and the like; sweetening agents; coloring agents; flavoring agents; antioxidants and the like; but not any anionic or nonionic surfactants. These additional ingredients can be present in amounts up to about 95% of the total composition weight. Selection of a particular ingredient or ingredients and the amounts used can be readily determined by one skilled in the art by reference to standard procedures and practices with respect to the particular tablet selected.

An especially preferred combination of ingredients in the tablet mixture includes the second active drug, either alone or in combination with pseudoephedrine or a pharmaceutically acceptable salt thereof, powdered cellulose, corn starch, sodium bicarbonate and magnesium stearate.

In a preferred embodiment of the present invention, the tablets are manufactured using an aqueous granulation.

(II) Extended-Release Pellets

The extended-release pellets of the present invention comprise a therapeutically effective amount of the pharmaceutical active ingredient, pseudoephedrine.

In a preferred embodiment where the pellet is coated, the pellet core comprises the active pseudoephedrine in an amount of about 30% to about 80% based on the total weight of the pellet core, and a binder such as microcrystalline cellulose or cornstarch in an amount of about 30% to about 50% based on the total weight of the pellet core.

In a preferred embodiment, the pellets comprise a polymer coating which controls the release of the pseudoephedrine therefrom. This coating is applied either from a solution and/or suspension in an organic solvent or from an aqueous coating mixture. Examples of suitable solvents include alcohols such as ethanol, methanol, isopropanol, and propanol, ketones such as acetone, and toluene. The application of the coating is performed in a fluidized bed or by pan coating; application in a fluidized bed is preferred.

The polymer coating comprises a water-soluble polymer and a water-insoluble polymer. The term "water-soluble polymer" as used herein includes polymers which are freely permeable to water, such as hydroxypropylcellulose. Likewise, the term "water-insoluble polymer" as used herein includes polymers which are slightly permeable to water, such as ethylcellulose. The ratio of water-soluble polymer to water-insoluble polymer is determined by the particular combination of polymers selected. Typically, however, the ratio of water-soluble polymer to water-insoluble polymer will be in the range of 1:2 to 1:20, preferably 1:8.8.

The water-soluble polymer is suitably polyvinylpyrrolidone, hydroxypropyl cellulose, hydroxypropyl methylcellulose, polyethylene glycol having a molecular weight of from 1700 to 20,000, or a mixture thereof. Preferably the water-soluble polymer is hydroxypropyl cellulose.

The water-insoluble polymer is suitably ethylcellulose, cellulose acetate phthlate, hydroxypropyl methylcellulose phthalate (HPMCP), polyvinyl acetate phthalate, methacrylic acid copolymer, hydroxypropyl methylcellulose acetate succinate, shellac, cellulose acetate trimellitate, or a mixture thereof. Preferably, the water-insoluble polymer is ethylcellulose.

Optionally the polymer coating may also include various excipients well known in the art, such as, for example, plasticizers, lubricants and fillers. Suitable plasticizers include triethyl citrate and other citrate esters, diethyl phthlate, tributyl citrate, and dibutyl sebacate, with triethyl citrate being preferred. Suitable lubricants include talc, titanium dioxide, glycerol monostearate, magnesium stearate and kaolin, with talc being preferred. Suitable fillers include silicon dioxide, titanium dioxide and magnesium stearate.

In a preferred embodiment the polymer coating contains by weight:

20–80% ethyl cellulose, more preferably 45–80%

1–10% hydroxypropyl cellulose, more preferably 3–8%

1–15% triethyl citrate, more preferably 5–10%

15–50% talc, more preferably 25–40% based on the total weight of the polymer coating.

In a preferred embodiment, the amount of the polymer coating will be about 5% to about 40% by weight, more preferably about 15% to about 25% by weight, based on the total weight of the pellets.

The extended-release pellets can be manufactured according to standard practices and procedures well known in the art. In a preferred embodiment the pellet cores are manufactured using an extrusion technique to produce a final core size of about 400–900 μm and the coating is then applied using a bottom spray fluid bed technique. By using the extrusion technique the cores produced are sufficiently robust to withstand the compressional forces experienced during tabletting.

In an alternate preferred embodiment, the pellet cores are manufactured such that they can be impacted yet allow the coat to deform. This can be achieved by having a core which comprises a homogenous mixture of pseudoephedrine and microcrystalline cellulose. Preferably at least 30% of the core weight is microcrystalline cellulose. The mechanism for the compaction of microcrystalline is well documented, and it is reported that extensive plastic flow occurs during compression due to numerous slip-planes and dislocations in its structure. This "movement" in the core is not critical to the performance of the pellets since the release of the active medicament is controlled by the pellet coating and not the core.

In another alternate embodiment, it is preferred to have pellets of a relatively small size to achieve close-packing in the tablets. Preferably the pellets have an average size of about 700 μm and a size range of about 500–850 μm.

EXAMPLE 1

Pellet Core Manufacture 770 g of pseudoephedrine hydrochloride crystals are homogeneously blended with 513 g of microcrystalline cellulose (AVICEL PH101). 245 g of purified water is then mixed with the blend to form a wet granulate which is subsequently extruded and spheronized to form cores about 500–710 μm in size.

The cores are then dried in a fluid bed dryer and sieved to a size range of about 500–710 μm.

Pellet Coating Formulation

A coating solution containing a) 80 g of ethylcellulose b) 9 g of hydroxypropyl cellulose c) 11 g of triethyl citrate d) 50 g of talc in 1500 g of ethanol is prepared.

The dried cores above are then Wurster coated using the coating solution above until a coat weight of about 10% (based on (a)+(b+(c) over the total pellet weight) is obtained.

The ingredients of the pharmaceutical composition according to the present invention are brought together into a tablet form for oral administration according to standard practices and procedures well known in the art of pharmaceutical science using conventional formulation and manufacturing techniques. For example, in a composition comprising terfenadine and pseudoephedrine, terfenadine is designed to be released immediately, while pseudoephedrine is split into two portions: 10 mg for immediate release and 110 mg for extended release. The composition is prepared in the following manner. First, the terfenadine, sodium bicarbonate, powdered cellulose, pseudoephedrine hydrochloride (the 10 mg/unit portion) and corn starch are mixed in a high-shear mixer-granulator, with the addition of water to form granules. These granules are dried in a fluid bed dryer and milled. The milled granules are then combined with pseudoephedrine pellets (the 110 mg/unit extended-release portion), talc, croscarmellose sodium, colloidal silicon dioxide and magnesium stearate in a V-type tumbler blender and mixed. Using a tablet press equipped with a force-feeder, the resultant blend is compressed into tablet cores having a hardness of 9–17 KP. The tablet cores may then be film-coated to yield the finished dosage form.

The final tablet composition thus comprises (in mg):

| | |
|---|---|
| Terfenadine | 60 |
| Pseudoephedrine Hydrochloride | 10 |
| Extended-Release Pseudoephedrine Pellets | 225 |
| Sodium Bicarbonate | 50 |
| Powdered Cellulose | 235 |
| Croscarmellose Sodium | 25.5 |
| Corn Starch | 235 |
| Talc | 2.5 |
| Colloidal Silicon Dioxide | 2 |
| Magnesium Stearate | 5 |
| Opadry II Yellow | 25 |
| Opadry II Clear | 12 |

In another embodiment, rather than being an ingredient in the tablet composition, the second active drug may optionally be sprayed-coated on the outside of the tablet to provide an immediate release layer. For example, a solution containing a mixture of the second active drug, optionally, pseudoephedrine, and one or more suitable additives may be sprayed on the outside of the tablet according to a method generally used in the art, such as fludized bed coating or pan coating. As the additives, the above-mentioned inert ingredients may be suitably used.

Dosage will vary according to the particular drug used in combination with pseudoephedrine. In general, the manufacturer's specifications for any drug or drug combination are useful guides to administration. *The Physician's Desk Reference* or other suitable publications can also be consulted to ascertain appropriate drug levels. Nonetheless, the typical adult dosage for a pharmaceutical composition comprising a combination of extended-release pseudoephedrine hydrochloride together with immediate release terfenadine and pseudoephedrine hydrochloride in accordance with Example 1, for the relief of symptoms associated with seasonal allergic rhinitis such as sneezing, rhinorrhea, pruritus, lacrimation and nasal congestion, is one tablet swallowed whole, morning and night.

The present invention is not limited by the embodiments described above which are presented as examples only, but can be modified in various ways within the scope of protection defined by the appended patent claims.

We claim:

1. A pharmaceutical tablet composition for oral administration comprising:

(a) a plurality of pellets, each pellet being about 300 to 1500 microns in size and having a core of pseudoephedrine, or a pharmaceutically acceptable salt thereof, in an amount from about 30% to about 80% by weight of the core, in association with a binder in an amount from about 30% to about 50% by weight of the core, and a coating surrounding the core, wherein the coating comprises a water-soluble polymer and a water-insoluble polymer, the ratio of the water-soluble polymer to the water-insoluble polymer being effective to provide an extended release of pseudoephedrine; and (b) a tablet mixture containing (i) a therapeutically effective amount of an active drug other than pseudoephedrine, including any pharmaceutically acceptable salt thereof, (ii) sodium bicarbonate in an amount from about 1% to about 15% by weight of the mixture, (iii) a powdered cellulose in an amount from about 10% to about 50% by weight of the mixture, (iv) optionally one or more inert ingredients, but not any anionic or nonionic surfactants, and (v) optionally a therapeutically effective amount of pseudoephedrine, or a pharmaceutically acceptable salt thereof, wherein the tablet mixture provides an immediate release of the active drug and of any pseudoephedrine, said tablet mixture having dispersed therein said plurality of pellets.

2. The tablet composition of claim 1, wherein the binder in the pellet core is microcrystalline cellulose or cornstarch.

3. The tablet composition of claim 1, wherein the active drug is an antihistamine.

4. The tablet composition of claim 3, wherein the antihistamine is selected from the group consisting of azatadine, loratadine, terfenadine, astemizole, chlorpheniramine, brompheniramine, acrivastine, hydroxyzine, pheniramine, diphenhydramine, mebhydroline, cyproheptadine, promethazine, dexchloropheniramine, cetirizine, triprolidine, and pharmaceutically acceptable salts thereof.

5. The tablet composition of claim 1, wherein the water-soluble polymer is selected from the group consisting of polyvinylpyrrolidone, hydroxypropyl cellulose, hydroxypropyl methylcellulose, polyethylene glycol having a molecular weight of from 1700 to 20,000, and mixtures thereof.

6. The tablet composition of claim 1, wherein the water-insoluble polymer is selected from the group consisting of ethylcellulose, cellulose acetate phthlate, hydroxypropyl methylcellulose phthalate, polyvinyl acetate phthalate, methacrylic acid copolymer, hydroxypropyl methylcellulose acetate succinate, shellac, cellulose acetate trimellitate, and mixtures thereof.

7. The tablet composition of claim 1, wherein the polymer coating further comprises a plasticizer and a lubricant.

8. A pharmaceutical tablet composition for oral administration comprising:
(a) a plurality of pellets, each pellet being about 300 to 1500 microns in size and having a core of pseudocphedrine, or a pharmaceutically acceptable salt thereof, in an amount from about 30% to about 80% by weight of the core, in association with a binder in an amount from about 30% to about 50% by weight of the core, and a coating surrounding the core, wherein the coating comprises a water-soluble polymer and a water-insoluble polymer, the ratio of the water-soluble polymer to the water-insoluble polymer being effective to provide an extended release of pseudoephedrine;
(b) a tablet mixture containing (i) sodium bicarbonate in an amount from about 1% to about 15% by weight of the mixture, (ii) a powdered cellulose in an amount from about 10% to about 50% by weight of the mixture, and (iii) optionally one or more inert ingredients, but not any anionic or nonionic surfactants, said tablet mixture having dispersed therein said plurality of pellets;

said pharmaceutial tablet composition further comprising
(c) an outer coating applied to said tablet mixture, said outer coating comprising (i) a therapeutically effective amount of an active drug other than pseudoephedrine, including any pharmaceutically acceptable salt thereof, (ii) one or more inert ingredients, but not any anionic or nonionic surfactants and (iii) optionally a therapeutically effective amount of pseudoephedrine, or a pharmaceutically acceptable salt thereof, wherein the outer coating provides an immediate release of the active drug and of any pseudoephedrine.

9. The tablet composition of claim 8, wherein the binder in the pellet core is microcrystalline cellulose or cornstarch.

10. The tablet composition of claim 8, wherein the active drug is an antihistamine.

11. The tablet composition of claim 10, wherein the antihistamine is selected from the group consisting of azatadine, loratadine, terfenadine, astemizole, chlorpheniramine, brompheniramine and acrivastine, hydroxyzine, pheniramine, diphenhydramine, mebhydroline, cyproheptadine, promethazine, dexchloropheniramine, cetirizine, triprolidine, and pharmaceutically acceptable salts thereof.

12. The tablet composition of claim 8, wherein the water-soluble polymer is selected from the group consisting of polyvinylpyrrolidone, hydroxypropyl cellulose, hydroxypropyl methylcellulose, polyethylene glycol having a molecular weight of from 1700 to 20,000, and mixtures thereof.

13. The tablet composition of claim 8, wherein the water-insoluble polymer is selected from the group consisting of ethylcellulose, cellulose acetate phthlate, hydroxypropyl methylcellulose phthalate, polyvinyl acetate phthalate, methacrylic acid copolymer, hydroxypropyl methylcellulose acetate succinate, shellac, cellulose acetate trimellitate, and mixtures thereof.

14. The tablet composition of claim 8, wherein the polymer coating further comprises a plasticizer and a lubricant.

* * * * *